(12) United States Patent
Olde et al.

(10) Patent No.: US 8,981,948 B2
(45) Date of Patent: Mar. 17, 2015

(54) ELECTRICAL CONNECTOR CLIP FOR MEDICAL SENSORS

(75) Inventors: Bo Olde, Lund (SE); Eddie Nilsson, Höör (SE); Derek White, Stockholm (SE); Thierry Court, Villeurbanne (FR); Eric Roussi, Caluire-et-Cuire (FR)

(73) Assignee: Gambro Lundia AB, Lund (SE)

( * ) Notice: Subject to any disclaimer, the term of this patent is extended or adjusted under 35 U.S.C. 154(b) by 778 days.

(21) Appl. No.: 13/322,984

(22) PCT Filed: May 29, 2009

(86) PCT No.: PCT/IB2009/005774
§ 371 (c)(1),
(2), (4) Date: Feb. 21, 2012

(87) PCT Pub. No.: WO2010/136837
PCT Pub. Date: Dec. 2, 2010

(65) Prior Publication Data
US 2012/0139734 A1    Jun. 7, 2012

(51) Int. Cl.
*G08B 21/00* (2006.01)
*A61B 5/04* (2006.01)
*A61F 2/02* (2006.01)
*A61M 37/00* (2006.01)
*A61M 31/00* (2006.01)
*A61B 5/0416* (2006.01)
*H01R 11/22* (2006.01)

(52) U.S. Cl.
CPC ......... *A61B 5/0416* (2013.01); *A61B 2562/227* (2013.01); *H01R 11/22* (2013.01); *H01R 2201/12* (2013.01)
USPC ............. 340/605; 340/635; 340/657; 600/30; 600/372; 600/382; 604/5.01; 604/503; 604/506

(58) Field of Classification Search
None
See application file for complete search history.

(56) References Cited

U.S. PATENT DOCUMENTS

| | | | |
|---|---|---|---|
| 4,938,712 A | 7/1990 | Black | |
| 5,593,385 A * | 1/1997 | Harrison et al. | ................ 604/83 |
| 5,947,910 A | 9/1999 | Zimmet | |
| 5,964,703 A | 10/1999 | Goodman et al. | |
| 6,152,754 A | 11/2000 | Gerhardt et al. | |
| 2002/0198483 A1 | 12/2002 | Wariar et al. | |

(Continued)

FOREIGN PATENT DOCUMENTS

| | | |
|---|---|---|
| WO | 99/15074 | 4/1999 |
| WO | 99/26686 | 6/1999 |

(Continued)

*Primary Examiner* — George Bugg
*Assistant Examiner* — Renee Dorsey
(74) *Attorney, Agent, or Firm* — K&L Gates LLP (57) ABSTRACT

A connector clip for medical sensors, including a first main body having two main tip contacts in electrical contact with electrical wires connectable to an instrument and a second main body mounted on the first main body and movable with respect to the first main body between an open position and a closed position. Two auxiliary tip contacts and an electric/electronic circuit provided with two connecting leads each electrically connected to one of the two auxiliary tip contacts are positioned in first or second main body. When a disposable sensor tab is correctly located and clamped each of two contacts is in contact with one of the main tip contacts and one of the auxiliary tip contacts and the electric circuit is connected in parallel with an electrical circuit defined by the sensor.

29 Claims, 8 Drawing Sheets

(56) References Cited

U.S. PATENT DOCUMENTS

2003/0004433 A1 1/2003 Hirschman
2004/0185709 A1 9/2004 Williams, Jr. et al.
2008/0004507 A1 1/2008 Williams, Jr. et al.

FOREIGN PATENT DOCUMENTS

| WO | 2005/054999 | 6/2005 |
| WO | 2005/076810 | 8/2005 |

* cited by examiner

ELECTRICAL CONNECTOR CLIP FOR MEDICAL SENSORS

RELATED APPLICATION

This application is the US national phase of international application PCT/IB32009/005774 filed 29 May 2009 which designated the U.S. and the entire contents of this application is hereby incorporated by reference.

BACKGROUND OF INVENTION

The present invention relates to an electrical connector clip for medical sensors, to a medical device comprising said clip and to a method for detecting blood leakage in extracorporeal blood treatments using said medical device.

In particular, the present invention relates to an electrical connector clip suitable for a sensor of an extravasation detection device and to an extravasation detection device comprising said connector.

During extra corporal blood treatments, such as dialysis and/or filtration treatment, accidental needle-fistula disconnection or blood leakage must be avoided. To this aim, a patch is attached to the body of the patient on or near the needle-fistula. The patch is a sheet sensor comprising two electrodes covered by an hydrophilic layer which may be located near the needle or below the arm. The electrodes are connected by means of cable to an alarm unit. In case of blood leakage, once sufficient blood is present inside the hydrophilic layer between the electrodes, the electrical properties of the sensor change and the alarm unit generates an alarm alerting the user. The electrical connection between the sensor and the cable is provided by a connector which allows the user to change the sheet sensor after each treatment.

Sheet sensor and connector of the type described above are known for example from document WO9926686. This document discloses a medical extravasation detection device comprising a sensor that can attach to the skin for sensing electrical information. Tissue impedance is calculated from the sensor signals. The patch has elongate pick-up electrodes inboard of elongate energizing electrodes. The presence of an extravasation is determined by interpreting the tissue impedance measurement. Sensor is provided with a coupling region shaped and dimensioned to fit within a clip. Clip is provided with electrical contacts positioned within the clip so that they can contact surface electrodes when conductor-patch is placed within clip. Clip has electrical leads which connect to a constant alternating current source of power and electrical leads which connects to voltage potential measuring circuitry. Clip further includes a first conduit housing leads which connects to a device which interprets the data sensed by sensor and a second conduit which connects to a CT injector. Conduit has capability to halt operation of injector in the event an extravasation has been detected or to convey this information to injector.

The applicant has found that known electrical connector clips can be improved in many aspects from the functional and structural points of view.

In particular, the applicant has found that the connectors of the known type do not play an operational role in detecting the above mentioned sensor electrical properties change due to blood leakage, since the signal coming from the sensor is entirely managed by the alarm unit.

In particular, the applicant has found that the connectors of the known type do not allow the alarm unit to verify that the above mentioned sensor is correctly inserted inside the connector and that the build up electrical circuit will allows to monitor the change due to blood leakage at the sensor level by the alarm unit.

Furthermore, the applicant has found that the connectors of the known type cannot assure the mechanical lock onto the sensor and cannot confirm the electrical connection of the sensor to the alarm unit.

It is also known from document U.S. Pat. No. 6,152,754 a circuit board based cable connector for use with a sensor connector tab to establish electrical signal connection between a sensor and a monitor or processor. The connector comprises a housing which encloses a circuit board. A slot is formed through a leading edge of the housing to allow insertion of the connector tab. A release mechanism releasable secures the connector tab within the housing. The circuit board is positioned adjacent and generally parallel to the inserted connector tab. Traces are formed on the side of the circuit board opposite the connector tab and establish electrical connection between wires of a cable and connector arms of the circuit board. The connector arms extend generally parallel to the circuit board and are bent at their free ends to form dips. Slots formed through the circuit board are adapted to receive the dipped contact arm ends. The contact arm dips extend through the slots and into contact with electrical contacts of the connector tab, establishing an electrical connection. Two of the contact arms are adapted to connect to the same sensor tab contact so that the arms electrically communicate with each other when the tab is inserted into the connector. The contact arms are in electrical communication only when the sensor tab is correctly inserted into the connector. Thus, the contact arms can be adapted to communicate a signal when the connector tab is correctly connected and can also be adapted to trigger an alarm to indicate an improper connection or to indicate that the connector tab has fallen out of the connector. This connector above described is structurally complex and expensive.

SUMMARY OF INVENTION

In this situation, the technical task at the basis of an embodiment of the present invention is to provide an electrical connector clip for medical sensors and to a medical device comprising said clip which should solve the drawbacks of the prior art mentioned above.

In particular, an object of an embodiment of the present invention is to provide an electrical connector clip for medical sensors allowing an alarm unit to efficiently detect blood leakage by monitoring the electrical properties of the sensor/cable/clip assembly.

A further object of an embodiment of the present invention is to provide an electrical connector clip for medical sensors capable of revealing the status of electrical connection between the sensor and an instrument to which the sensor is attached. This electrical connection status being a way to detect the correctly location and orientation of the sensor inside the clip.

A further object of an embodiment of the present invention is to propose an electrical connector clip for medical sensors which should assure the right and easy coupling (electrical and mechanical) between the sensor and the clip.

A further object of an embodiment of the present invention is to propose an electrical connector clip for medical sensors which should be reliable and at the same time structurally simple, easy to clean and cheap to manufacture.

The above specified objects are substantially achieved by an electrical connector clip for medical sensors and to a medical device comprising said clip, comprising the technical features described in one or more of the annexed claims.

In particular, according to a first aspect, an embodiment of the present invention relates to an electrical connector clip for medical sensors, comprising:

a first main body having at least two main tip contacts in electrical contact with electrical wires connectable to an instrument;

a second main body mounted on the first main body and movable with respect to the first main body between an open position and a closed position;

at least two auxiliary tip contacts electrically insulated from the main tip contacts and positioned in first main body or in the second main body;

an electric circuit positioned in first main body or in the second main body and provided with at least two connecting leads each electrically connected to one of the auxiliary tip contacts;

wherein in the closed position, when a disposable sensor end is clamped between the first and second main bodies, each of at least two contacts on said sensor end is in contact with one of the main tip contacts and one of the auxiliary tip contacts and the electric circuit is connected in parallel with an electrical circuit defined by the sensor.

According to an embodiment, the sensor end is shaped as a tab and the sensor is, for instance, a patch probe.

The electric circuit is an electric component chosen, for instance, from the group comprising: a resistor, an impedance, a capacitor.

The electric circuit comprises a light emitting device, for instance a LED, or a sound emitting device.

According to an embodiment, said main and auxiliary tip contacts are positioned close to an edge of the first main body According to an embodiment, said main and auxiliary tip contacts are aligned along a path parallel to said edge.

According to an embodiment, at least one of the main tip contacts is closer to the edge than the auxiliary tip contacts.

Otherwise, at least one of the main tip contacts is farther from the edge than the auxiliary tip contacts.

According to an embodiment, the second main body comprises one or more conductive elements placed on a second surface facing the first surface; said conductive element or elements, when the clip is closed without any sensor end in between, short circuiting at least one of the main tip contacts and/or the auxiliary tip contacts.

According to an embodiment, the electrical connector clip further comprises an additional electrical circuit connected to said two or more conductive elements. This additional electrical circuit is not the one which is connected to the auxiliary tip contacts.

According to an embodiment, this additional electrical circuit comprises a visual indicator, as another light emitting device, for instance a LED, and provides a signal when the end of the sensor is not correctly inserted into the clip.

According to an embodiment, the electrical connector clip further comprises an additional electrical component connected between the two main electrical conductors and providing to the instrument an univocal electrical signature without any disposable sensor end inserted and another information when a disposable sensor end is inserted.

According to an embodiment, this additional electrical component could comprise a visual indicator, as another light emitting device, for instance a LED, fully independent of the sensor electrical circuit.

According to an embodiment, the main tip contacts, the auxiliary tip contacts and the electric circuit are done with a Printed Circuit Board (PCB) integrated inside the clip or with stamped over moulded contact comb.

According to an embodiment, the first main body and/or the second main body comprise at least one projection engageable with at least one hole or recess in the sensor end.

According to an embodiment, the first main body and/or the second main body comprise at least a guide ridge aligned along a direction of insertion of the sensor end in the clip.

In particular, the first main body and/or the second main body comprise a central guide ridge aligned along a direction of insertion of the sensor end in the clip and engageable in a slot of said sensor end.

According to an embodiment, the first main body and/or the second main body present an asymmetric structure to engage an asymmetric sensor end.

In particular, the central guide ridge is shifted towards one of the side of the clip and the tab presents a corresponding asymmetric shape.

According to an embodiment, the light of the light emitting devices cited above (belonging to the electric circuit or to the additional electrical circuit or to the additional electrical component) is visible through the second main body and/or installed on the second main body.

According to an embodiment, the first main body and the second main body are each an injected plastic piece.

According to an embodiment, the first main body and the second main body are formed by one injected plastic piece only.

According to an embodiment, the second main body includes a leaf spring.

According to an embodiment, a weakened portion connects the first main body to the second main body.

According to an embodiment, the electrical connector clip further comprises releasable coupling means operatively interposed between the first main body and the second main body.

According to a second aspect, an embodiment of the present invention relates to a medical device comprising: a disposable sensor to be applied to a patient, an instrument connected to the sensor to monitor a parameter and an electrical connector clip as above described, to connect the sensor to the instrument.

According to an embodiment, said device is an extravasation detection device, the sensor is an electrode patch and the instrument is an alarm unit.

According to a third aspect, an embodiment of the present invention relates to a method for detecting blood leakage in extra corporal blood treatments, comprising the following steps:

preparing an extravasation detection device as above described;

applying the sensor to the body of a patient on or near a needle-fistula used in an extra-corporal blood treatment;

connecting the sensor end of the sensor to the electrical connector clip;

verifying by the alarm unit that the sensor end of the sensor is correctly setup to the electrical connector clip and notifying the situation to the user;

monitoring by means of the alarm unit a voltage between two wires electrically connected at least to the main tip contacts;

emitting by means of the alarm unit an alarm signal when the monitored voltage is lower than a first threshold because blood leakage occurs.

emitting by means of the alarm unit an alarm signal when the monitored voltage indicate that the sensor isn't anymore correctly setup to the electrical connector clip.

The monitored voltage is lower than the first threshold when the sensor end is not in the clip and short circuiting occurs by means of the conductive element or elements.

According to an embodiment, the monitored voltage is higher than at least a second threshold when at least one of the following situations occurs:

the sensor end is not in the clip and no conductive element is present;

the sensor end is wrongly set up in the clip;

a failure of the electric circuit happens.

According to an embodiment, the monitored voltage equals a predetermined fixed value, depending on clip circuit, when the sensor end is correctly inserted into the clip and the sensor is dry.

According to an embodiment, when the sensor tab is correctly inserted into the clip, the LED of the electric circuit and/or of the additional device managed by an electrical circuit fully independent from the sensor one is/are on. When the sensor tab is out of the clip, the LED of the additional electric circuit is on.

SUMMARY OF THE DRAWINGS

Further features and advantages of the present invention will appear more clearly from the exemplary and thus non limiting description of a preferred but non exclusive embodiment of an electrical connector clip for medical sensors and to a medical device comprising said clip, as illustrated in the annexed drawings, wherein.

DETAILED DESCRIPTION OF INVENTION

In the annexed figures, reference numeral 1 indicates an electrical connector clip according to an embodiment of the present invention belonging to a medical device 2 according to an embodiment of the present invention.

Figure 1:
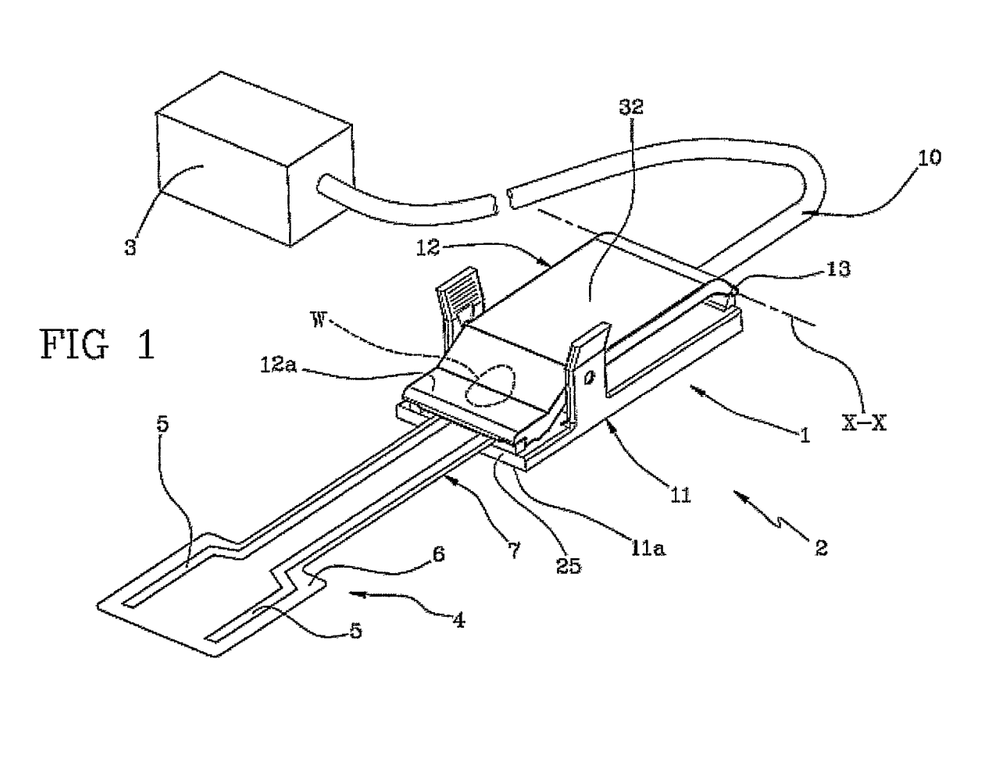
FIG. 1 shows a perspective view of a medical device comprising an electrical connector clip for medical sensors according to the invention in a closed configuration.

The medical device 2 shown in FIG. 1 is an extravasation detection device which comprises an instrument 3, or alarm unit, electrically connected to a disposable electrode patch 4 (sensor).

Figure 2:
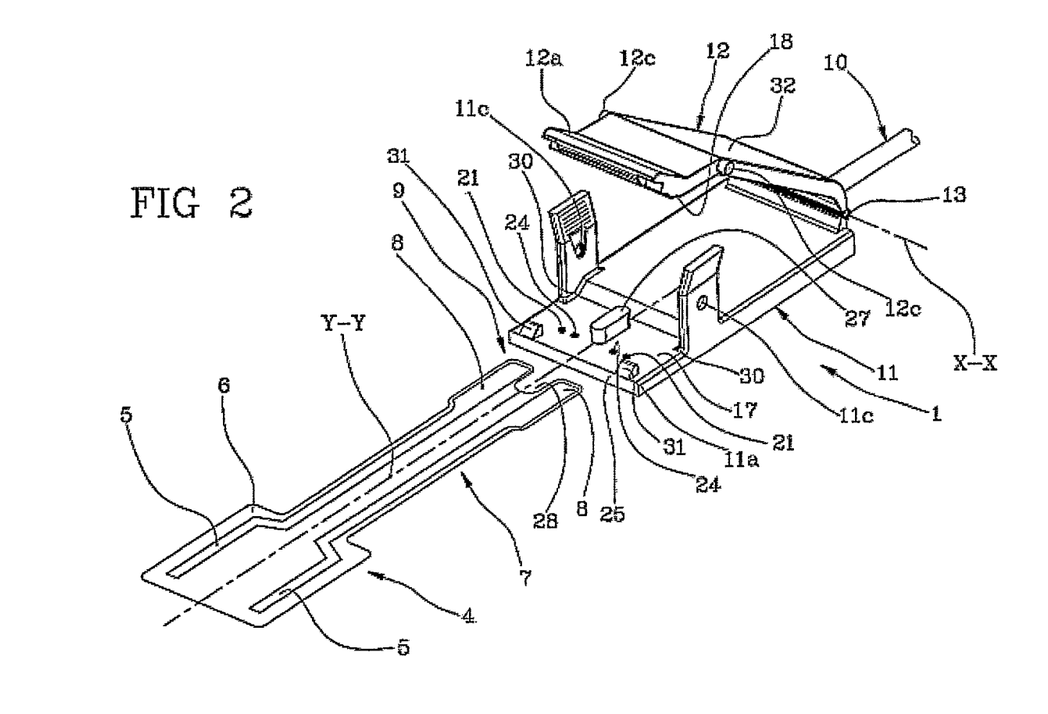
FIG. 2 shows a perspective view of the sensor and of the clip of FIG. 1 when the clip is an open configuration and the sensor is disengaged from the clip.

The electrode patch 4 comprises, on one of its sides, two electrodes 5 covered on the larger proximal area by a layer of hydrophilic material (not shown). Each electrode is defined by a strip of conductive material laid on an isolating substrate 6. The two strips 5 are parallel and spaced one from the other and extends endlessly on a tab 7 made by the same isolating material of the patch 4. Each strips 5 presents a tip contact area 8 placed on an end 9 of the tab 7 opposite the patch 4 (FIG. 2).

Figure 4:
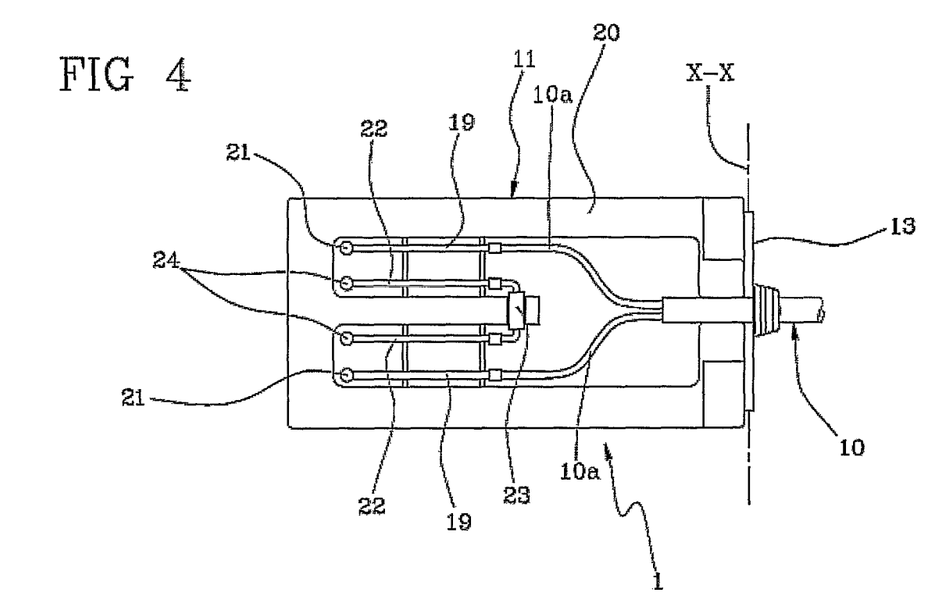
FIG. 4 shows a bottom view of the clip of FIGS. 1 to 3.

The alarm unit 3 comprises a circuitry, not shown, electrically connected to the two electrodes 5 by means of a twin cable 10 with two wires 10a and the connector clip 1 (FIGS. 1 and 4).

The circuitry is able to measure the electrical properties of the sensor. In case of blood leakage, once sufficient blood is present between the electrodes, the electrical properties of the sensor 4 change and the alarm unit 3 generates an alarm alerting the user.

Figure 3:
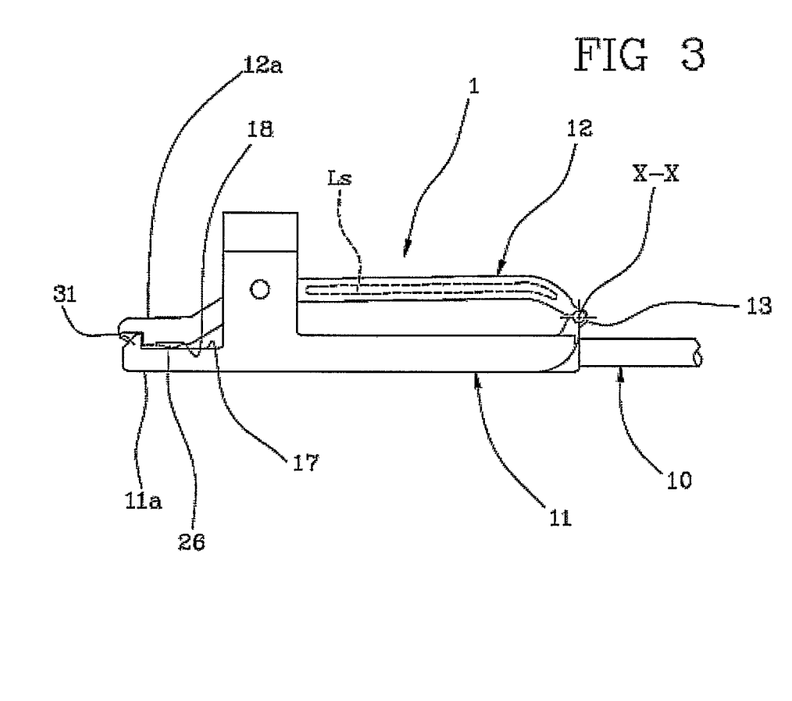
FIG. 3 shows a side elevation view of the clip of FIGS. 1 and 2 in the closed configuration.
Figure 3A:
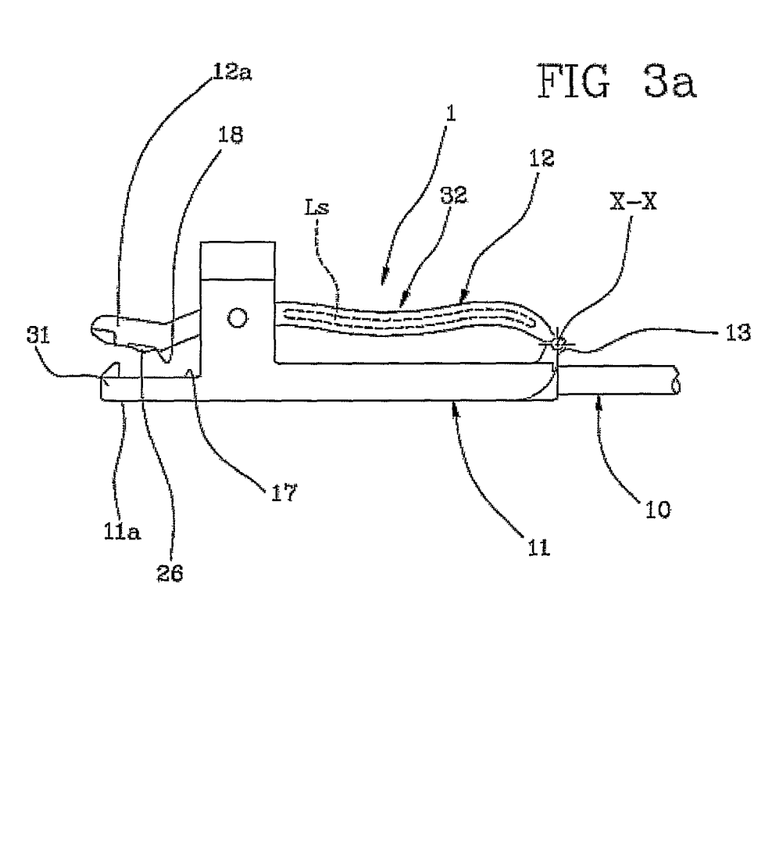
FIG. 3a shows a side elevation view of the clip of FIGS. 1 and 2 in the closed configuration with a force applied to the handling portion in order to deform the second main body and thereby separate the front portions.

The electrical connector clip 1 comprises a first main body 11 and a second main body 12 mounted on the first main body and movable with respect to the first main body 11 between an open position and a closed position. The first and second main bodies 11, 12 are able to rotate one with respect to the other around a rotation axis X-X in order to facilitate cleaning in the open position. In the closed position, front portions 11a, 12a of the bodies 11, 12 are placed one against the other to hold in between the end 9 of the sensor tab 7 (FIGS. 1 and 3). The first main body 11 and/or the second main body 12 can comprise ridges, pins or projections clamping the tab 7 to retain the tab 7 and/or damage the tab area to prevent re-use of the electrode patch 4.

In a first embodiment, shown in FIGS. 1 to 6a, the first and second main bodies 11, 12 are made by a single piece of moulded plastic material, allowing a fast and cheap production. The two bodies 11, 12 are connected by a weakened portion 13 extending along the rotation axis X-X in proximity of a rear end of the clip 1. The second main body 12 comprises side pins 12c (FIG. 2) engaging into recesses 11c of the first main body 11 to hold the bodies 11, 12 in the closed position. The pins 12c and recesses 11c defines releasable coupling means operatively interposed between the first main body 11 and the second main body 12. The second main body 12 may be attached to a leaf spring "L" or include a leaf spring in its structure.

Figure 7:
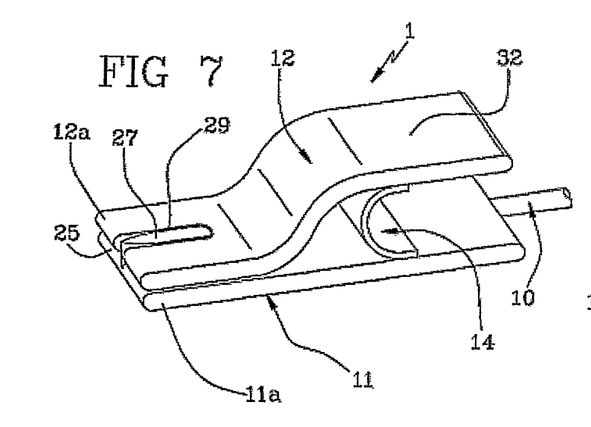
FIG. 7 shows a perspective view of another embodiment of the clip of the invention.
Figure 8:
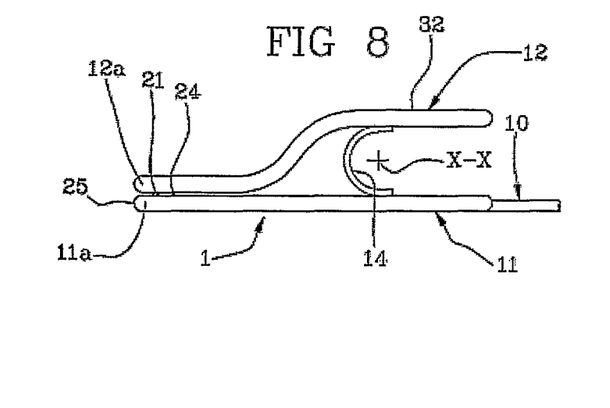
FIG. 8 shows a side view of the clip of FIG. 7.

In a second embodiment, shown in FIGS. 7 and 8, each of the first and second main bodies 11, 12 is made by a piece of moulded plastic material and connected by means of a leaf spring 14. The leaf spring 14 is U-shaped and mounted in a intermediate zone of the bodies 11, 12.

Figure 9:
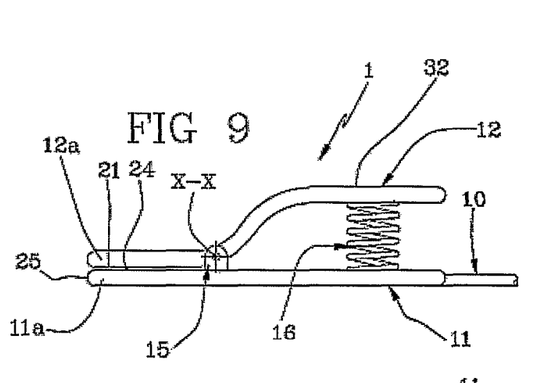
FIG. 9 shows a side view of the clip of another embodiment of the clip of the invention.

In a third embodiment, shown in FIG. 9, each of the first and second main bodies 11, 12 is made by a piece of moulded plastic material and connected by means of a hinge 15. A coil spring 16 is interposed between rear portions 11b, 12b of the bodies 11, 12.

In the second and third embodiments the springs 14, 16 push the front portion 11a of the first main body 11 against the front portion 12a of the second main body 12 to retain the tab 7. In the second embodiment (FIGS. 7 and 8) the leaf spring 14 performs the double function of connecting the bodies 11, 12 and closing the clip 1.

The first main body 11 presents a first surface 17 (FIGS. 2 and 3, 6 and 6a) facing a first surface 18 (FIGS. 2, 3 and 5) of the second main body 12.

The first main body 11 carries two main electrical conductors 19 in electrical contact with the wires 10a of the cable 10 (FIG. 4). In particular, as shown in the attached figures, the two main electrical conductors 19 are installed in a recess on a second surface 20 of the first main body 11 opposite the first surface 17. The recess could be closed by a cover, not shown, or filled with an appropriate sealant or potting material. Alternatively the wires 10a, the cable 10, the two main electrical conductors 19, main tip contacts 21, the auxiliary conductors 22, the circuit 23 and the auxiliary tip contacts 24 can all be over moulded by the injection moulded first main body 11 or the single piece injection moulded first main body 11 second main body 12.

The cable 10 enters the first main body 11 through an aperture on a rear end of the clip 1 and the two main electrical conductors 19 extends to the front portion 11a of the first main body 11 where they pass through the thickness of said front portion 11a and open onto the first surface 17 with main tip contacts 21 (FIGS. 2, 5, 6 and 6a).

The first main body 11 carries also two auxiliary conductors 22 electrically insulated from the two main electrical conductors 19 which, in the preferred embodiments, are installed in the recess on the second surface 20 (FIG. 4). A resistor 23 is mounted in the recess and is provided with two connecting leads each electrically connected to one of the two auxiliary electrical conductors 22. The two auxiliary electrical conductors 22 pass through the thickness of the front portion 11a and open onto the first surface 17 with auxiliary tip contacts 24 (FIGS. 2, 5, 6, 6a). Instead of the resistor 23, another electric/electronic component or circuit 23 could be chosen. Said electric component 23 is a light emitting device, for instance a LED (light emitting diode), or a sound emitting device. The light emitting device could be visible through the second main body 12 by means of a window or a transparent portion.

According to an embodiment not shown, the clip 1 comprises an additional electrical component connected between the two main electrical conductors 19. This additional electrical component provides to the alarm unit 3 an univocal electrical signature when no disposable sensor tab 7 is inserted in the clip 1.

The alarm unit 3 is able to recognize the kind of clip 1 used. The same additional electrical component provides to the alarm unit 3 another electrical information when the disposable sensor tab 7 is inserted in the clip 1 and electrically connected to the two main electrical conductors 19. This additional electrical component in a preferred embodiment comprises a visual indicator, as another light emitting device, for instance a LED, which is fully independent of the sensor electrical circuit. Also this further light emitting device could be visible through the second main body 12 by means of a window or a transparent portion.

All the components, contacts and cable wire can be done with a small Printed Circuit Board (PCB) integrated inside the clip or with stamped over moulded contact comb.

In the embodiment shown in FIGS. 1 to 6, the four tip contacts 21, 24 are aligned along a path parallel and close to the front edge 25. The main tip contacts 21 lie external and close to a side border of the first main body 11.

Figure 6:
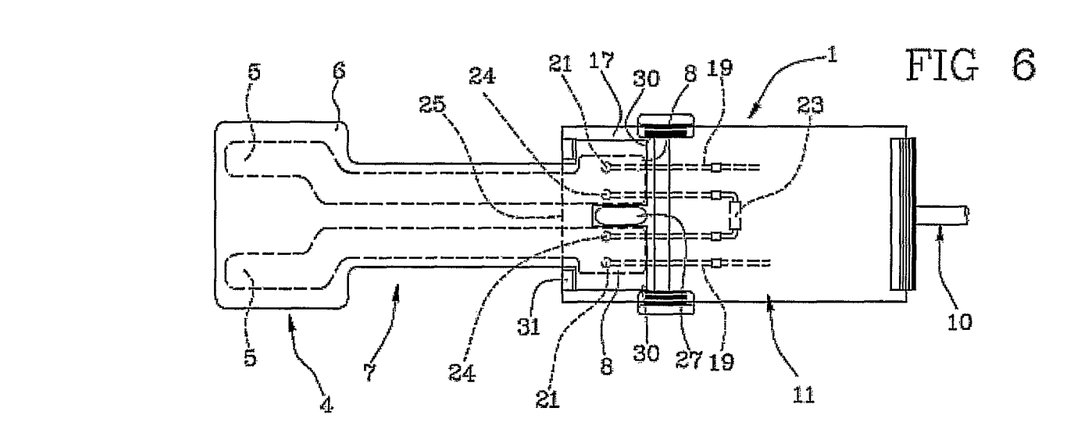
FIG. 6 shows a top view of the sensor and of the clip of FIG. 1 with a portion removed to better show other features.
Figure 6A:
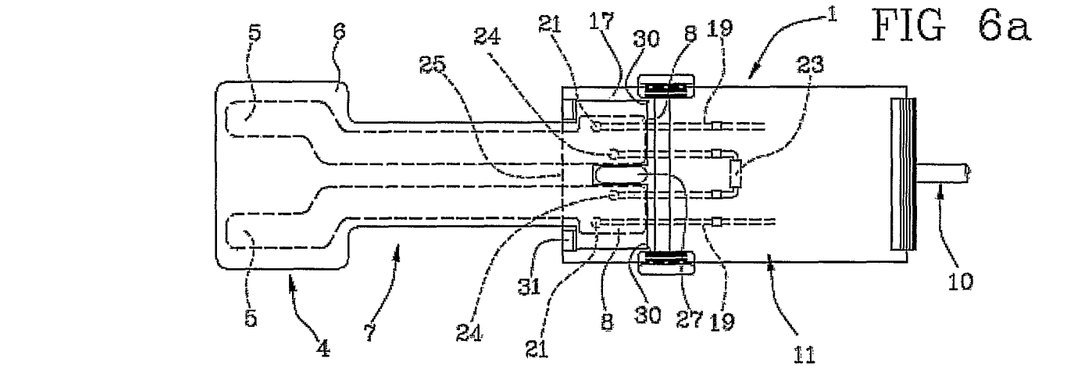
FIG. 6a shows a top view of the sensor and a variation of the clip of FIG. 1 with a portion removed to better show other features.

In the embodiment shown in FIG. 6a, the main tip contacts 21 are closer to a front edge 25 of the first main body 11 with respect to the two auxiliary tip contacts 24. The four tip contacts 21, 24 are disposed on vertexes of a isosceles trapezium with the bigger side close to the front edge 25. Each main tip contact 21 is close to a side edge of the first main body 11.

In other embodiments, not shown, the positions of the four tip contacts 21, 24 could also be reversed or the four tip contacts 21, 24 could be positioned on vertexes of a rectangle.

Figure 5:
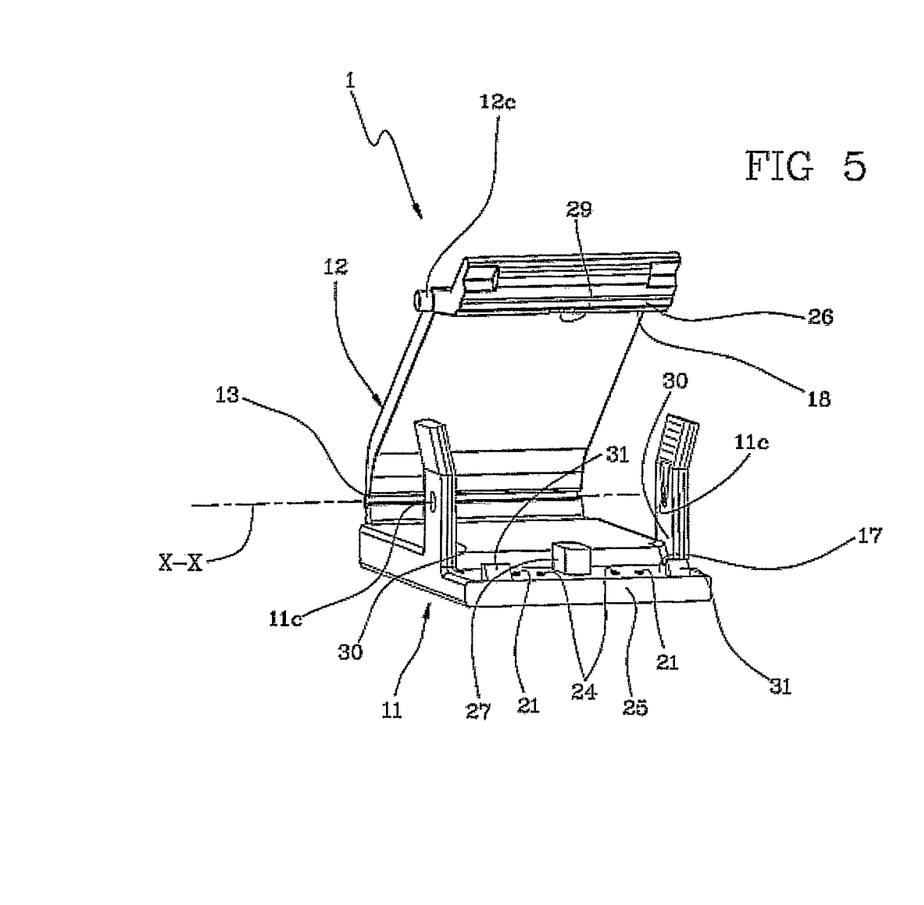
FIG. 5 shows an additional perspective view of the clip of FIG. 2 in the open configuration.

The clip 1 further comprises a conductive element 26, i.e. a plate like element, placed on the second surface 18 facing the first surface 17 (FIGS. 3 and 5). The conductive element 26, when the clip 1 is closed without any sensor tab 7 in between, short circuits the main electrical conductors 19 and/or the auxiliary conductors 22. In preferred embodiments, the conductive element 26, in the above cited closed position of the clip 1, electrically connect all the four main and auxiliary tips 21, 24. The conductive element 26 may alternatively comprise two or more conductive plates connected to one or more electronic components or circuits.

According to an embodiment not shown, the clip 1 comprises an additional electrical circuit connected to the conductive element 26. This additional electrical circuit in a preferred embodiment comprises a visual indicator, as another light emitting device, for instance a LED. Also this further light emitting device could be visible through the second main body 12 by means of a window or a transparent portion. This further light emitting device could be also installed on said second main body 12.

The clip 1 according to the present invention comprises mechanical guides capable of guiding the sensor tab 7 into the clip 1 in the correct position. Said mechanical guides comprises a central guide ridge 27 aligned along a direction of insertion "Y-Y" of the sensor tab 7 in the clip 1. The central guide ridge 27, as shown in the attached figures, is located on the first surface 17 of the first main body 11 near the front edge 25. The central guide ridge 27, as shown in the attached figures, extends in a plane of symmetry of the clip 1.

The sensor tab 7 presents a slot 28 opening on the end 9 of the tab 7 (FIG. 2) and extending along the direction of insertion "Y-Y". The slot 28, as shown in the attached figures, extends in a plane of symmetry of the tab 7. When the tab 7 is placed into the clip 1, the central guide ridge 27 is engaged into the slot 28. Furthermore, when the clip 1 is closed, the central guide ridge 27 engages into a recess 29 shaped in the first surface 18 of the second main body 12 (FIG. 5).

The mechanical guides can also comprise side guide ridges 30 which in the clip 1 shown in attached FIGS. 1 to 6a are embodied by lateral protrusions placed on the first main body 11 and carrying the recesses 11c for the side pins 12c. When the tab 7 is placed into the clip 1, said tab 7 is placed between the side guide ridges 30 and the side borders of the tab 7 are in contact with the side guide ridges 30.

In a further embodiment, not shown, the mechanical guides comprise a projection engageable in a hole in the sensor tab 7. This kind of guide is also a locking which prevents the tab 7 to slip out of the clip 1.

In other different embodiments, not shown, the mechanical guides 27, 30 could be placed on the second main body 12 or both on the first and second main bodies 11, 12.

Figure 10:
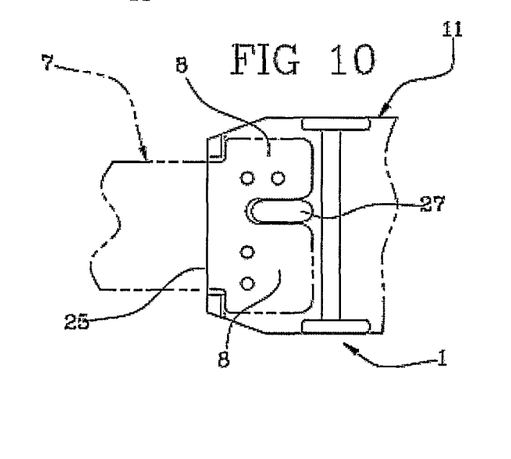
FIG. 10 shows a top view of the sensor and of a portion of another variation of the clip of FIG. 1.

In some embodiments, one of which shown schematically in FIG. 10, the mechanical guides 27, 30 are asymmetric in order to avoid the tab 7 to be inserted upside-down. In FIG. 10, the central guide ridge 27 is shifted laterally and the tab 7 presents a corresponding asymmetrical shape.

The shape and structure of the clip and in particular of the mechanical guides as above described could be part of the present invention also with or without the electrical structure of the clip 1. It is also part of an embodiment of the present invention an electrical connector clip for medical sensors, comprising: a first main body having two main tip contacts in electrical contact with electrical wires connectable to an instrument; a second main body mounted on the first main body and movable with respect to the first main body between an open position and a closed position; plus one or more of the additional features introduced in claims 10 to 14 and 16 to 18.

In use, with reference to the embodiment of FIGS. 1 to 6, with the clip 1 in the closed position, a force is applied to the handling portion 32 in order to deform the second main body 12 and thereby separate front portion 11a from front portion 12a. The end 9 of the tab 7 of the sensor 4 is placed on the front edge 25 of the first main body 11 and pushed towards the rear end of the clip 1. The tab 7 slides on inclined protrusions 31 and on the first surface 17. Meanwhile, the central guide ridge 27 enters the slot 28. The tab 7 slides until the central guide ridge 27 stops against the inner part of the slot 28.

The central and side guide ridges 27, 30 avoid any misalignment of the tab 7 with respect to the clip 1 and to the contacts 21, 24 on the clip 1. The inclined protrusions 31 avoid the slipping out of the tab 7.

Once reached the stop position, each of the tip contact area 8 of the sensor 4 lies on one of the main tip contacts 21 and on one of the auxiliary tip contacts 24 (FIGS. 6, 6a and 10).

Indeed, the tip contact area 8 of the tab 7 is an area of un-insulated conductive material provided with a contact area large enough to cover both the main and auxiliary tip contacts 21, 24. In this configuration, the electric component 23 is connected in parallel with the electrical circuit defined by the sensor 4.

Then, the front portions 11a and 12a of clip 1 are closed by releasing the force on the handling portion 32 on the second main body 12 to clamp the tab 7 and retain the same in a locked position.

In the second and third embodiment of FIGS. 7 and 9 in order to insert the tab 7, the clip 1 must be open exerting a force on the handling portion 32 in contrast to the force of the spring 14, 16.

In the closed configuration, the alarm unit 3 is able to detect electrical property changes due to blood leakage.

The electrical component or circuit inside the clip 1 acts as an electrical component or circuit connected in parallel with the electrical circuit defined by the sensor 4.

If this electrical component or circuit is a resistor, the impedance "Rass" viewed by the alarm unit 3 at the two wires 10a can be considered as one single equivalent variable resistor the value of which depends on sensor 4 status (Rs) and clip resistor 23 (Rclip).

The measuring of said impedance "Rass" is done by monitoring the voltage "V" between the two wires 10a. When the tab 7 is correctly inserted into the clip 1 and the sensor 4 is dry, "Rass" is substantially equal to "Rclip" and the voltage "V" is substantially equal to a fixed value "Vok".

When the sensor is wet (blood detection) or when the two wires of the cable or some clip contacts are abnormally short-circuited, "V" descends below a predetermined first threshold "V1", close to zero, and an alarm signal is emitted by the control unit 3.

When the sensor is not inserted (open circuit) and the conductive element 26 is not present, "V" rises over a second threshold "V2" and equals a voltage defined by the alarm unit 3 internal resistor network for limiting voltage. The same happens if the sensor tab 7 is wrongly set up in the clip 1 or there is a failure of the electric circuit 23.

In the preferred embodiment comprising as electric component a visual or audio indicator, when the tab 7 is correctly inserted into the clip 1, said indicator is powered and provides to the user a clear indication of said correct insertion. It may also give indication of accidental detachment.

In the preferred embodiment comprising the additional electrical component connected between the two main electrical conductors 19 and comprising a further visual indicator, when the tab 7 is correctly inserted into the clip 1, said indicator is powered and provides to the user a clear indication of said correct insertion. It may also give indication of accidental detachment. In the preferred embodiment comprising the conductive element 26 placed on a second surface 18 facing the first surface 17, when the tab 7 is not present, the short circuiting bridge provides indication of detachment if the sensor is fully removed without the need for secondary contacts and related circuit.

In the preferred embodiment comprising the additional electrical circuit connected to the conductive element 26 and a further visual indicator, when the tab 7 is not correctly inserted into the clip 1, said indicator is powered and provides to the user a clear indication of accidental detachment.

In the preferred embodiments wherein the main tip contacts 21 are closer to a front edge 25 of the first main body 11 with respect to the two auxiliary tip contacts 24 or vice-versa, the partial insertion of the tab 7 into the clip 1 is indicated. If the main tip contacts 21 are closer to a front edge 25 of the first main body 11 with respect to the two auxiliary tip contacts 24 and the sensor 4 is not fully inserted, anyway the alarm unit 3 is able to notify when the sensor 4 is wetted by blood.

The invention claimed is:

1. An electrical connector clip for a medical sensor, the clip comprising:
    a first main body including at least two main tip contacts in electrical contact with electrical wires connectable to an instrument;
    a second main body mounted on the first main body and movable with respect to the first main body between an open position and a closed position;
    at least two auxiliary tip contacts electrically insulated from the main tip contacts and positioned in first main body or in the second main body; and
    an electric circuit positioned in first main body or in the second main body and provided with at least two connecting leads each electrically connected to one of the auxiliary tip contacts;
    wherein in the closed position, when a disposable sensor end is clamped between the first and second main bodies, each of at least two contacts on said sensor end is in contact with one of the main tip contacts and one of the auxiliary tip contacts and the electric circuit is connected in parallel with an electrical circuit defined by the sensor.

2. The electrical connector clip according to claim 1, wherein the electric circuit is an electric component including at least one of a resistor, an impedance, and a capacitor.

3. The electrical connector clip according to claim 1, wherein the electric circuit comprises at least one of a light emitting device and a sound emitting device.

4. The electrical connector clip according to claim 1, wherein said main and auxiliary tip contacts are positioned close to an edge of the first main body.

5. The electrical connector clip according to claim 1, wherein said main and auxiliary tip contacts are aligned along a path parallel to said edge.

6. The electrical connector clip according to claim 4, wherein at least one of the main tip contacts is closer to the edge than the auxiliary tip contacts.

7. The electrical connector clip according to claim 4, wherein at least one of the main tip contacts is farther from the edge than the auxiliary tip contacts.

8. The electrical connector clip according to claim 1, wherein the second main body comprises at least one conductive element placed on a second surface facing the first surface; said at least one conductive element, when the clip is closed without any sensor end in between, short circuiting at least one of the main tip contacts and the auxiliary tip contacts.

9. The electrical connector clip according to claim 1, further comprising an additional electrical circuit connected to said two or more conductive elements and providing a signal when the end of the sensor is not correctly inserted into the clip.

10. The electrical connector clip according to claim 1, further comprising an additional electrical component connected between the two main electrical conductors and providing to the instrument an univocal electrical signature without any disposable sensor end inserted and another information when a disposable sensor end is inserted.

11. The electrical connector clip according to claim 1, wherein the main tip contacts, the auxiliary tip contacts and the electric circuit are mounted on a Printed Circuit Board (PCB) inside the clip or with stamped over moulded contact comb.

12. The electrical connector clip according to claim 1, wherein at least one of the first main body and the second main body comprise a projection engageable in a hole or recess in the sensor end.

13. The electrical connector clip according to claim 1, wherein at least one of the first main body and the second main body comprises a guide ridge aligned along a direction of insertion of the sensor end in the clip.

14. The electrical connector clip according to claim 1, wherein at least one of the first main body and the second main body comprise a central guide ridge aligned along a direction of insertion of the sensor end in the clip and engageable in a slot of said sensor end.

15. The electrical connector clip according to claim 1, wherein at least one of the first main body and the second main body includes an asymmetric structure which engages an asymmetric sensor end.

16. The electrical connector clip according to claim 14, wherein the central guide ridge is offset towards one of the side of the clip and the end presents a corresponding asymmetric shape.

17. The electrical connector clip according to claim 3, wherein the electrical circuit includes the light emitting device, the which emits a light visible through the second main body.

18. The electrical connector clip according to claim 1, wherein the first main body and the second main body are each an injected molded plastic piece.

19. The electrical connector clip according to claim 1, wherein the first main body and the second main body are formed as an integrated injected molded plastic piece.

20. The electrical connector clip according to claim 1, wherein the second main body includes a leaf spring.

21. The electrical connector clip according to claim 18, wherein a weakened portion connects the first main body to the second main body.

22. The electrical connector clip according to one claim 1, further comprising releasable coupling operatively interposed between the first main body and the second main body.

23. A medical device comprising:
a disposable sensor to be applied to a patient,
an instrument connected to the sensor to monitor a parameter and
an electrical connector clip configured to connect the sensor to the instrument, the clip comprising:
a first main body including main tip contacts each in electrical contact with the instrument;
a second main body on the first main body and movable with respect to the first main body between an open position and a closed position;
auxiliary tip contacts electrically insulated from the main tip contacts and positioned in first main body or in the second main body;
an electric circuit in the first main body or in the second main body, and including connecting leads each electrically connected to one of the auxiliary tip contacts, and
wherein in the closed position, when a disposable sensor end is clamped between the first and second main bodies, each of at least two contacts on said sensor end is in contact with both one of the main tip contacts and one of the auxiliary tip contacts and the electric circuit is connected in parallel with an electrical circuit defined by the sensor.

24. The medical device of claim 23, wherein said device is an extravasation detection device, the sensor is an electrode patch and the instrument is an alarm unit.

25. A method for detecting blood leakage in extra corporal blood treatments comprising:
connecting an extravasation detection device to an electrical connector clip;
applying an electrode patch to the body of a patient proximate to a needle-fistula, wherein the patch comprises a sensor with contacts;
connecting the contacts of the sensor of the electrode patch to the electrical connector clip having main tip contacts and auxiliary tip contacts, wherein the contacts of the sensor are each configured to connect to one of main tip contacts and one of the auxiliary tip electrical contacts;
monitoring by an alarm unit of a voltage between the main tip contacts after the connection of the contacts of the sensor to the electrical connector clip, and
emitting by the alarm unit an alarm signal if the monitored voltage (V) is lower than a first threshold (V1), wherein the alarm signal indicates blood leakage.

26. The method of claim 25, wherein the monitored voltage (V) is lower than the first threshold (V1) when the sensor end is not in the clip and short circuiting occurs by a conductive element or elements in the clip and electrically coupled to the auxiliary tip contacts.

27. The method of claim 25, wherein the monitored voltage (V) is higher than at least a second threshold (V2) when at least one of the following situations occurs: the sensor end is not in the clip and no conductive element is present; the sensor end is wrongly set up in the clip; a failure of the electric circuit.

28. The method of claim 25, wherein the monitored voltage (V) equals a predetermined fixed value (Vok), depending on the clip circuit, when the sensor contacts are correctly inserted into the clip and the sensor contacts are dry.

29. The method of claim 25, wherein, when the sensor end is correctly inserted into the clip, a light emitting device is on.

* * * * *